(12) United States Patent
Winter

(10) Patent No.: US 8,148,564 B2
(45) Date of Patent: Apr. 3, 2012

(54) COMPOUNDS FOR FORMING METAL NITRIDES

(75) Inventor: Charles H. Winter, Bloomfield Hills, MI (US)

(73) Assignee: Wayne State University, Detroit, MI (US)

( * ) Notice: Subject to any disclaimer, the term of this patent is extended or adjusted under 35 U.S.C. 154(b) by 516 days.

(21) Appl. No.: 12/438,451

(22) PCT Filed: Aug. 30, 2007

(86) PCT No.: PCT/US2007/077261
§ 371 (c)(1),
(2), (4) Date: Feb. 23, 2009

(87) PCT Pub. No.: WO2008/028053
PCT Pub. Date: Mar. 6, 2008

(65) Prior Publication Data
US 2010/0239765 A1   Sep. 23, 2010

Related U.S. Application Data

(60) Provisional application No. 60/841,122, filed on Aug. 30, 2006.

(51) Int. Cl.
*C07F 11/00* (2006.01)
(52) U.S. Cl. .............. 556/57; 556/51; 556/52; 548/101; 427/255.394
(58) Field of Classification Search .................. 556/51, 556/52, 57; 548/101; 427/255.394
See application file for complete search history.

(56) References Cited

U.S. PATENT DOCUMENTS

2002/0000199 A1   1/2002   Harada
2006/0068101 A1   3/2006   Machida et al.

OTHER PUBLICATIONS

Baxter et al., "Molecular Routes to Metal Carbides, Nitrides, and Oxides. 2. Studies of Ammonolysis of Metal Dialkylamides and Hexamethylsisylamides," Chem. Mater., 1996, v. 8, n. 6, pp. 1222-1228.
Leskela, M. et al., "Atomic Layer Deposition Chemistry: Recent Developments and Future Chalennges," Angew. Chem. Int. Ed. 2003, 42, pp. 5548-5554.
Paivasaari, J., et al., "Atomic Layer Deposition of Rate Earth Oxides," Topics Appl. Physics 106, 2007, pp. 15-32.
Dezelah, C.L. et al., "Atomic Layer Deposition of Tungsten(III) Oxide Thin Films from W2(NMe2)6 and Water: Precursor-Based Control of Oxidation State in the Thin Film Material," J. Am. Chem. Soc. 2006, 128, pp. 9638-9639.
Dezelah, C.L. et al., "Atomic Layer Deposition of Ga2O3 Films from a Dialkylamido-Based Precursor," Chem. Mater. , 2006, 18, pp. 471-475.
Putkonen, M. et al., "Organometallic Precursors for Atomic Layer Deposition," Top Organomet Chem (2005) 9: 125-145.

*Primary Examiner* — Porfirio Nazario Gonzalez
(74) *Attorney, Agent, or Firm* — Brooks Kushman P.C.

(57) ABSTRACT

Nitride forming precursors are heated to form a metal nitride on a substrate. In some variations, the precursors are contacted with the substrate which has previously been heated to a sufficient temperature to form a nitride film. Precursors to tungsten and molybdenum nitride are provided.

15 Claims, 4 Drawing Sheets

COMPOUNDS FOR FORMING METAL NITRIDES

CROSS-REFERENCE TO RELATED APPLICATIONS

This application claims the benefit of U.S. provisional application Ser. No. 60/841,122 filed 30 Aug. 2006, the disclosure of which is incorporated in its entirety by reference herein.

BACKGROUND OF THE INVENTION

1. Field of the Invention

The present invention is related to compounds and methods for pyrolytically forming metal nitrides, and in particular, the present invention is related to compounds and methods for pyrolytically forming tungsten nitride and molybdenum nitride.

2. Background Art

Tungsten nitride ($WN_x$, x=0.5-1.0) and related carbonitride phases are promising barrier materials for copper metallization in future microelectronics devices. For device applications, barrier material films must be grown in narrow (<65 nm) and deep features with perfect conformal coverage. In addition, very thin (<10 nm), defect-free films are required. Of the many possible thin film growth methods, atomic layer deposition ("ALD") has been identified as one of the most promising manufacturing techniques for future microelectronics devices, since it can provide thin films with controlled thickness as well as perfect conformal coverage. ALD film growth entails exposure of the substrate surface to sequential pulses of two or more precursors, which are separated by inert gas purges to remove excess precursor and also to remove the reaction byproducts. To have maximum utility in ALD growth, a metal-containing precursor must be thermally stable on the surface of the substrate at the film growth temperature, but also must react rapidly and efficiently with a second reagent to provide the desired material.

While recent studies have described several different metalorganic precursors for the chemical vapor deposition (CVD) growth of $WN_x$ films, the viability of these precursors in ALD processes is uncertain due to the requirements of excellent thermal stability and high reactivity toward ammonia in ALD growth. Most ALD processes for $WN_x$ and tungsten carbonitride films have employed $WF_6$ and ammonia. However, use of $WF_6$ leads to evolution of HF during the growth chemistry, which can etch substrate and reactor surfaces and can cause integration problems due to surface fluorine deposits. As a result, there is significant interest in the development of metalorganic precursors for tungsten nitride films, since they should avoid problems with hydrogen halide formation and halogen incorporation.

There have been two reported metalorganic ALD precursors to $WN_x$. The ALD process involving $W(NtBu)_2(NMe_2)_2$ and ammonia afforded $WN_x$ films between 250-350° C. The deposition was self-limiting in both ammonia and $W(NtBu)_2(NMe_2)_2$, but the growth rate increased with temperature between 250-350° C. We have recently reported the ALD growth of tungsten carbonitride films between 400-450° C. using $W(NtBu)_2(tBu_2pz)_2$ ($tBu_2pz$=3,5-di-tert-butylpyrazolato) and ammonia. This process exhibited self-limiting ALD growth between 400-450° C., but also showed an increase in growth rate with increasing temperature. In CVD growth, $W(CO)_6$ and ammonia afforded $WN_x$ films at temperatures as low as 200° C., while tungsten(VI) precursors of the formula $W(NR)Cl_4(CH_3CN)$ gave $WN_x$ films with ammonia only at 450° C. or higher. Such a trend suggested to us that mid- and low-valent tungsten complexes might afford ALD growth of $WN_x$ films at lower temperatures than are possible with the two previously reported tungsten(VI) ALD precursors. $W(CO)_6$ is unlikely to be a useful ALD precursor, due to thermal decomposition through loss of carbonyl ligands at low temperatures.

Accordingly, there is a need for improved processes and precursors for making nitride materials.

SUMMARY OF THE INVENTION

The present invention solves one or more problems of the prior art by providing in at least one embodiment compounds that are useful for the pyrolytic formation of metal nitrides such as tungsten nitride and molybdenum nitride. The compounds of this embodiment is described by either formula 1 or 2:

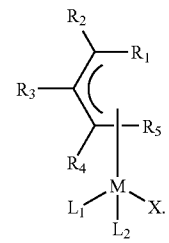

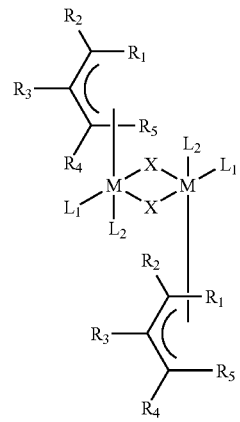

wherein $R_1$, $R_2$, $R_3$, $R_4$, and $R_5$ are each independently alkyl, aryl, arylalkyl, hydrogen, and silyl;

$L_1$, $L_2$ are each independently a neutral donor ligand;

X is a monoanionic nitrogen donor ligand; and

M is molybdenum or tungsten.

In another embodiment of the present invention, compounds that are useful for the pyrolytic formation of metal nitrides such as tungsten nitride and molybdenum nitride are provided. The compounds of this embodiment is described by either formula 7 or 8:

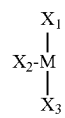

-continued $$X_2-\overset{\overset{X_1}{|}}{M}\equiv\overset{\overset{X_1}{|}}{M}-X_2$$
$$\overset{|}{X_3}\quad\overset{|}{X_3}$$

8 wherein:

$X_1$, $X_2$, and $X_3$ are each independently a monoanionic nitrogen donor ligand; and M is molybdenum or tungsten.

In other embodiments of the present invention, methods for making a metal nitride coating on a substrate are provided. The methods of these embodiments comprise heating a compound having formulae 1, 2, 7 or 8 or $W_2(NMe_2)_6$ to a sufficient temperature to form the metal nitride coating. In a refinement of these embodiments, the compound having formula 1, 2, 7 or 8 or $W_2(NMe_2)_6$ or a byproduct thereof is reacted with a nitrogen source during the step of heating to a sufficient temperature.

In still other embodiments of the present invention, methods for making a metal nitride coating on a substrate are provided. The methods of these embodiments comprise contacting the substrate with a compound having formulae 1, 2, 7, or 8 or $W_2(NMe_2)_6$. Typically, the substrates are heated to a sufficient temperature to form the metal nitride coating prior to contact with the compound.

DETAILED DESCRIPTION OF THE PREFERRED EMBODIMENT(S)

Figure 1:
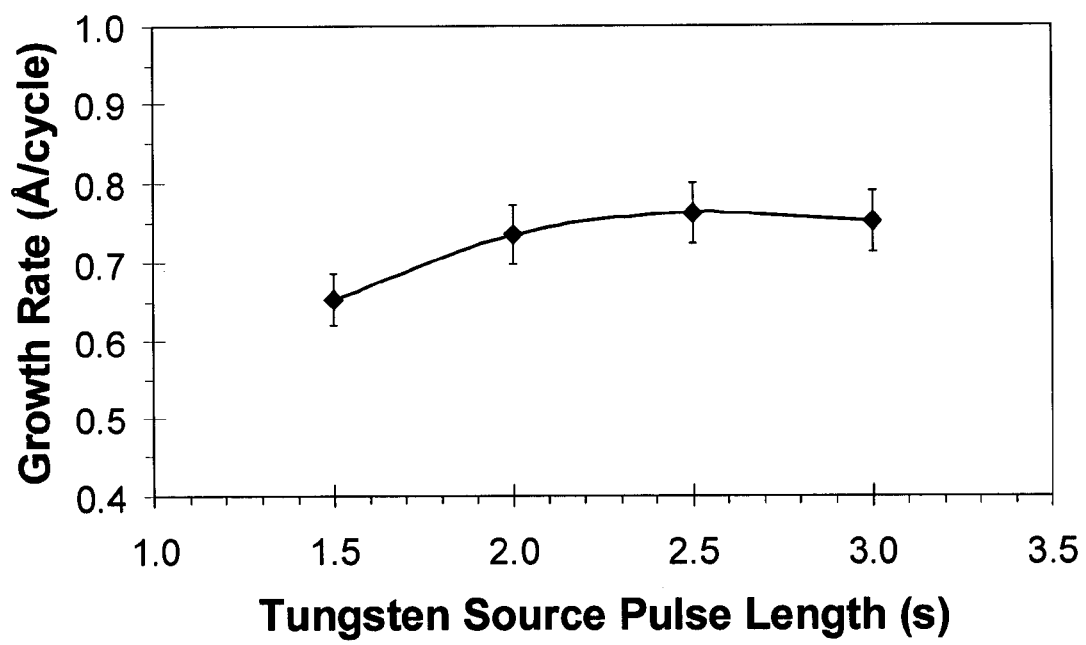
FIG. 1 provides a plot showing the influence of tungsten precursor pulse length on WNx growth rate for films deposited at 180° C. using a 1.5 second ("s") ammonia pulse.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. The description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application in their entirety to more fully describe the state of the art to which this invention pertains.

In an embodiment of the present invention, a compound useful for the formation of a metal nitride is provided. The compound of this embodiment is described by formula 1 or 2:

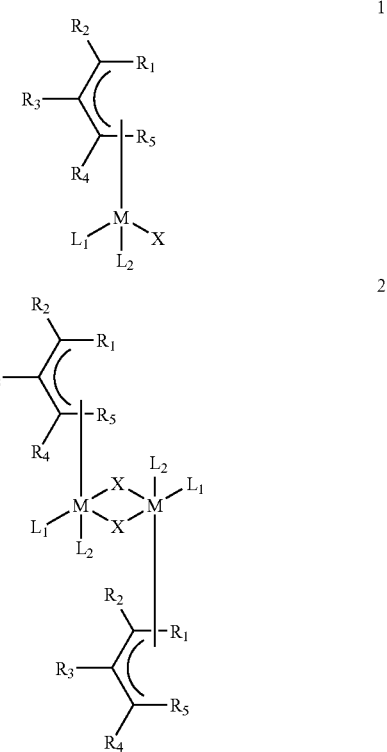

wherein $R_1$, $R_2$, $R_3$, $R_4$, and $R_5$ are each independently alkyl, aryl, arylalkyl, hydrogen, and silyl;

$L_1$, $L_2$ are each independently a neutral donor ligand;

X is a monoanionic nitrogen donor ligand; and

M is molybdenum or tungsten.

In a variation of this embodiment, $R_1$, $R_2$, $R_3$, $R_4$, and $R_5$ are each independently alkyl or hydrogen. In another variation, $R_1$, $R_2$, $R_3$, $R_4$, and $R_5$ are each hydrogen. In yet another variation, $L_1$, $L_2$ are each carbon monoxide. In still another variation X is:

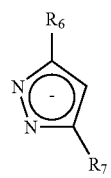

3

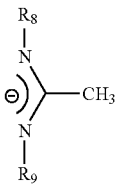

4

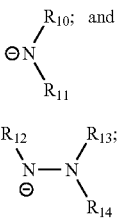

5

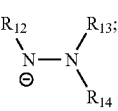

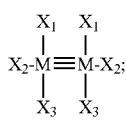

6

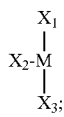

wherein $R_6$, $R_7$, $R_8$, $R_9$, $R_{10}$, $R_{11}$, $R_{12}$, $R_{13}$, and $R_{14}$ are each independently hydrogen or alkyl. In a variation of the present embodiment, $R_6$, $R_7$, $R_8$, $R_9$, $R_{10}$, $R_{11}$, $R_{12}$, $R_{13}$, and $R_{14}$ are hydrogen. In still another variation of the present embodiment, $R_6$, $R_7$, $R_8$, $R_9$, $R_{10}$, $R_{11}$, $R_{12}$, $R_{13}$, and $R_{14}$ are each independently hydrogen, —$CF_3$, isopropyl, or t-butyl.

In another embodiment of the present invention, compounds that are useful for the pyrolytic formation of metal nitrides such as tungsten nitride and molybdenum nitride are provided. The compounds of this embodiment are described by either formula 7 or 8:

$$X_2-M\equiv M-X_2$$
(with $X_1$, $X_3$ substituents; formula 7)

$$X_2-M$$
(with $X_1$, $X_3$ substituents; formula 8)

wherein:

$X_1$, $X_2$, and $X_3$ are each independently a monoanionic nitrogen donor ligand; and M is molybdenum or tungsten.

In a variation of the present embodiment, $X_1$, $X_2$, and $X_3$ are each independently:

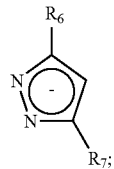

3

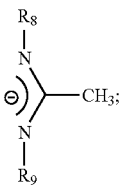

4

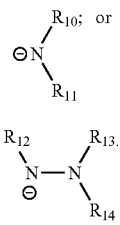

5

6 wherein $R_6$, $R_7$, $R_8$, $R_9$, $R_{10}$, $R_{11}$, $R_{12}$, $R_{13}$, and $R_{14}$ are each independently hydrogen or alkyl. In another embodiment, $R_6$, $R_7$, $R_8$, $R_9$, $R_{10}$, $R_{11}$, $R_{12}$, $R_{13}$, and $R_{14}$ are hydrogen. In still another embodiment, $R_6$, $R_7$, $R_8$, $R_9$, $R_{10}$, $R_{11}$, $R_{12}$, $R_{13}$, and $R_{14}$ are each independently hydrogen, —$CF_3$, isopropyl, or t-butyl.

In yet another embodiment of the present invention, a method for making a metal nitride coating on a substrate is provided. The method of this embodiment comprises heating a compound having formulae 1 or 2 as set forth above to a sufficient temperature to form the metal nitride coating. In one refinement, the sufficient temperature is from 25° C. to 1000° C. In another refinement, the sufficient temperature is from 150° C. to 300° C. In a variation of this embodiment, the compound having formula 1 or 2 or a byproduct thereof is reacted with a nitrogen source during the step of heating to a sufficient temperature. Suitable nitrogen sources include, but are not limited to, ammonia, amines, hydrazine, alkyl substituted hydrogen hydrazines, dinitrogen ($N_2$), or combinations thereof. In another variation of the present embodiment, the step of heating is performed at about atmospheric pressure or at a reduced pressure. In one refinement, the pressure is from about $10^{-6}$ torr to 760 torr. In another refinement, the pressure is from about 0.1 torr to 1 torr.

In yet another embodiment of the present invention, a method for making a metal nitride coating on a substrate is provided. The method of this embodiment comprises contacting the substrate with a compound having formula 1 or 2. Typically, the substrate is heated to a sufficient temperature to form the metal nitride coating prior to contact with the compound having formula 1 or 2. In one refinement, the sufficient temperature is from 25° C. to 1000° C. In another refinement, the sufficient temperature is from 150° C. to 300° C. In a variation of the present embodiment, the substrate is contacted with a nitrogen source prior to the step of contacting the substrate with a compound having formulae 1 or 2. In another variation of the present embodiment, the step of heating is performed at about atmospheric pressure or at a reduced pressure. In one refinement, the pressure is from about $10^{-6}$ torr to 760 torr. In another refinement, the pressure is from about 0.1 torr to 1 torr.

In yet another embodiment of the present invention, a method for making a metal nitride coating on a substrate is provided. The method of this embodiment comprising heating a compound having formula 7 or 8 as set forth above to a sufficient temperature to form the metal nitride coating. In one refinement, the sufficient temperature is from 25° C. to 1000° C. In another refinement, the sufficient temperature is from 150° C. to 300° C. In a variation of this embodiment, the compound having formula 7 or 8 or a byproduct thereof is reacted with a nitrogen source during the step of heating to a sufficient temperature. Suitable nitrogen sources include, but are not limited to, ammonia, amines, hydrazine, alkyl substituted hydrogen hydrazines, dinitrogen ($N_2$), or combinations thereof. In another variation of the present embodiment, the step of heating is performed at about atmospheric pressure or at a reduced pressure. In one refinement, the pressure is from about $10^{-6}$ torr to 760 torr. In another refinement, the pressure is from about 0.1 torr to 1 torr.

In yet another embodiment of the present invention, a method for making a metal nitride coating on a substrate is provided. The method of this embodiment comprises contacting the substrate with a compound having formula 7 or 8. Typically, the substrate is heated to a sufficient temperature to form the metal nitride coating prior to contact with the compound having formula 7 or 8. In one refinement, the sufficient temperature is from 25° C. to 1000° C. In another refinement, the sufficient temperature is from 150° C. to 300° C. In a variation of the present embodiment, the substrate is contacted with a nitrogen source prior to or subsequent to the step of contacting the substrate with a compound having formula 7 or 8. In another variation of this embodiment, the step of heating is formed from substantially atmospheric pressure or at a reduced pressure. In one refinement, the pressure is from about $10^{-6}$ torr to 760 torr. In another refinement, the pressure is from about 0.1 torr to 1 torr.

In still another embodiment of the present invention, a method for making a tungsten nitride coating on a substrate is provided. The method of this embodiment comprises heating a compound having formula $W_2(NMe_2)_6$ to a sufficient temperature to form the metal nitride coating. In one refinement, the sufficient temperature is from 25° C. to 1000° C. In another refinement, the sufficient temperature is from 150° C. to 300° C. In a refinement of this embodiment, the compound having formula $W_2(NMe_2)_6$ or a byproduct thereof is reacted with a nitrogen source during the step of heating to a sufficient temperature. Suitable nitrogen sources include, but are not limited to, is ammonia, amines, hydrazine, alkyl substituted hydrogen hydrazines, dinitrogen ($N_2$), or combinations thereof. In another variation of the present embodiment, the step of heating is performed at about from atmospheric pressure or at a reduced pressure. In one refinement, the pressure is from about $10^{-6}$ torr to 760 torr. In another refinement, the pressure is from about 0.1 torr to 1 torr.

In still another embodiment of the present invention, a method for making a metal nitride coating on a substrate is provided. The method of this embodiment comprises contacting the substrate with a compound having formula $W_2(NMe_2)_6$. Typically, the substrate is heated to a sufficient temperature to form the metal nitride coating prior to contact with the compound having formula $W_2(NMe_2)_6$. In one refinement, the sufficient temperature is from 25° C. to 1000° C. In another refinement, the sufficient temperature is from 150° C. to 300° C. In a refinement of this variation, the substrate is contacted with a nitrogen source prior to the step of contacting the substrate with a compound having formula $W_2(NMe_2)_6$. In another refinement, the step of heating is performed at about atmospheric pressure or at a reduced pressure. In one refinement, the pressure is from about $10^{-6}$ torr to 760 torr. In another refinement, the pressure is from about 0.1 torr to 1 torr.

The following examples illustrate the various embodiments of the present invention. Those skilled in the art will recognize many variations that are within the spirit of the present invention and scope of the claims.

1. Tungsten Nitride Thin Films by Atomic Layer Deposition

Precursor Properties. The precursor $W_2(NMe_2)_6$ was prepared in 40-45% yields on 20 gram scales according to a literature procedure. (Chisholm, M. H.; Martin, J. D. Inorg. Synth. 1992, 29, 137). This complex was purified by sublimation at 120° C./0.05 Torr in a horizontal glass tube, in which one end of the tube was placed in a Buchi Kugelrohr oven as the heat source and the other end was attached to the vacuum source. Pure $W_2(NMe_2)_6$ collected as a yellow solid just outside of the oven at the start of the cool portion of the glass tube. In preparative sublimations (~0.8 g), there was <0.5% residue left after sublimation and $W_2(NMe_2)_6$ was collected in 85-90% recovered yields. $W_2(NMe_2)_6$ is air sensitive, and was handled under dry nitrogen or argon atmospheres at all times. In the solid state, $W_2(NMe_2)_6$ does not melt, but darkens at about 230° C. in a sealed capillary tube under argon.

$WN_x$ Film Growth Studies. The deposition of $WN_x$ thin films by ALD was studied using $W_2(NMe_2)_6$ as the tungsten source compound and ammonia as the nitrogen source. Experimental parameters such as precursor pulse length, substrate temperature, and the number of deposition cycles were varied to assess the growth behavior. The film growth rate was investigated as a function of $W_2(NMe_2)_6$ pulse length at a deposition temperature of 180° C. (FIG. 1). The number of deposition cycles, the ammonia pulse length, and the length of the purge following the ammonia pulse were held constant at 800, 1.5 seconds, and 3.0 seconds, respectively. The length of the purge following the tungsten precursor pulse was kept equal to the length of the tungsten precursor pulse. The growth rate was constant at about 0.74 Å/cycle for $W_2(NMe_2)_6$ pulse lengths of greater than 2.0 seconds. With a 1.5 second pulse of $W_2(NMe_2)_6$, a slight decrease in the growth rate was observed. A central feature of ALD growth is the saturation of the substrate surface with each precursor pulse. When this condition is satisfied, growth is self-limited and doses beyond the minimal amount necessary for formation of a monolayer on the surface do not result in an increase in growth rate. From the observed behavior it is evident that a $W_2(NMe_2)_6$ pulse length of 2.0 seconds affords surface-limited growth. Shorter pulses of $W_2(NMe_2)_6$ resulted in sub-saturative growth and lower growth rates.

Figure 2:
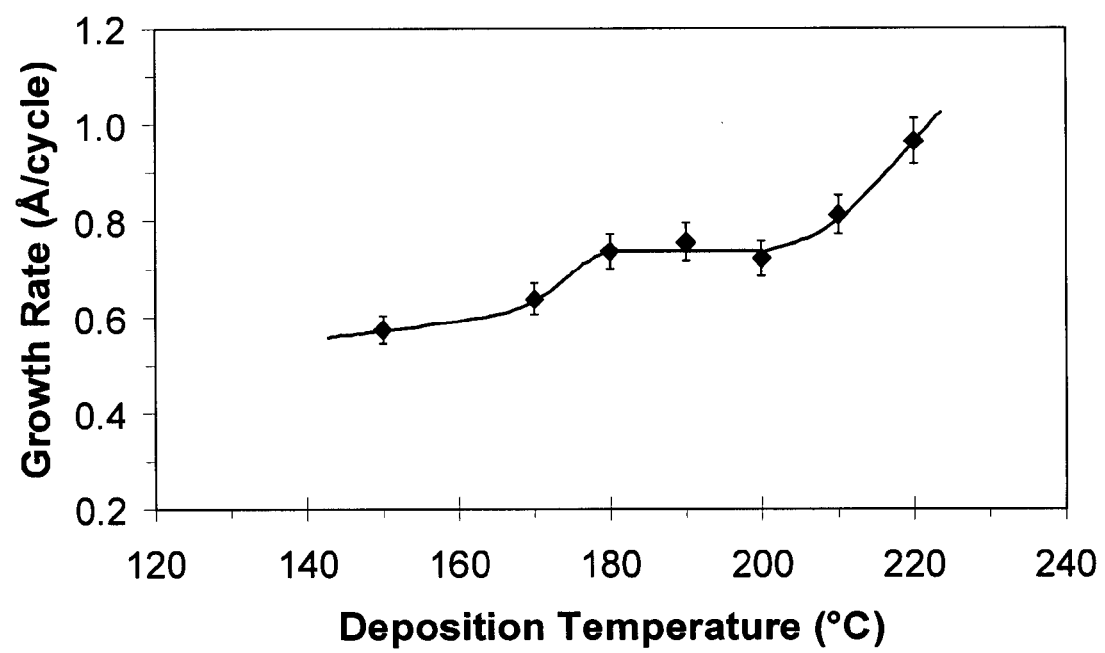
FIG. 2 provides a plot showing the influence of deposition temperature on WNx growth rate for films deposited using a 2.0 second tungsten precursor pulse and a 1.5 second ammonia pulse.

The growth rate was also investigated as a function of deposition temperature (FIG. 2). Depositions in this set of experiments were carried out using $W_2(NMe_2)_6$ and ammonia pulse lengths of 2.0 seconds and 1.5 seconds, respectively, a 2.0 second purge following the tungsten precursor pulse, a 3.0 second purge following the ammonia pulse, and 800 deposition cycles. The growth rates ranged between 0.74 and 0.81 Å/cycle for substrate temperatures between 180 and 210° C. These growth rates are identical within the experimental uncertainty associated with the film thickness measurements. Observation of an ALD window is a common feature of many ALD processes. Growth rates of 0.57, 0.66, and 0.96 Å/cycle were observed outside of the ALD window at substrate temperatures of 150, 170, and 220° C., respectively.

Figure 3:
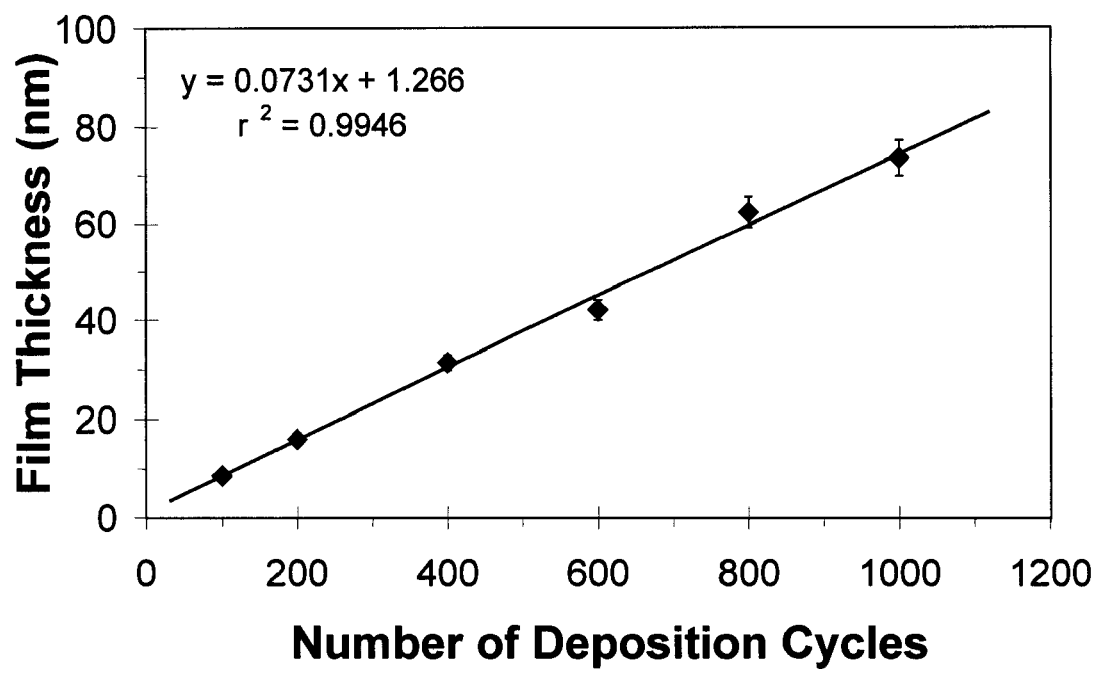
FIG. 3 provides film thickness as a function of the number of deposition cycles for WNx films deposited at 180° C. using tungsten precursor and ammonia pulse lengths of 2.0 and 1.5 seconds, respectively.

FIG. 3 shows a plot of film thickness versus the number of deposition cycles. At a temperature of 180° C. and with $W_2(NMe_2)_6$ and ammonia pulse lengths of 2.0 seconds and 1.5 seconds, respectively, the film thicknesses varied linearly with the number of deposition cycles. A linear regression of the data points resulted in an excellent fit ($r^2$=0.9946), a slope (m=0.731 Å/cycle) that closely resembles the measured growth rate, and a y-intercept that approaches the origin (y-intercept=1.27 nm). Additionally, a deposition of 800 cycles at 180° C. with a tungsten precursor pulse length of 2.0 seconds was performed without an ammonia pulse. No detectable film growth was observed under these conditions. Thus, film formation proceeds only in the presence of ammonia, which excludes film growth through thermal self-decomposition of $W_2(NMe_2)_6$.

Film Characterization. Time-of-flight elastic recoil detection analysis (TOF-ERDA) was performed on representative tungsten nitride films to determine the elemental compositions (Table 1). The films were found to be air-sensitive, which led to the rapid incorporation of oxygen unless preventative measures were employed. To reduce the possibility of air exposure, the tungsten nitride films were coated with a 50 nm thick layer of ALD-grown AlN deposited from sequential pulses of trimethylaluminum and ammonia. The ratio of tungsten to nitrogen was 1.20, 1.35, and 1.20 for films deposited at 150, 180, and 210° C., respectively. These values are similar within experimental uncertainty, and indicate a slightly nitrogen-rich phase relative to $W_2N$. The carbon, hydrogen, and oxygen concentrations were also measured for films deposited from $W_2(NMe_2)_6$ and ammonia at 150, 180, and 210° C. The concentration of carbon increased with deposition temperatures, with carbon to tungsten ratios of 0.13, 0.20, and 0.33 at 150, 180, and 210° C., respectively. Hydrogen levels decreased with increasing temperature, as demonstrated by hydrogen to tungsten ratios of 0.33, 0.28, and 0.23 at 150, 180, and 210° C., respectively. Oxygen to tungsten ratios were 0.26, 0.33, and 0.18 at 150, 180, and 210° C., respectively. Depth profiling was performed in all TOF-ERDA analyses to investigate any possible compositional variation as a function of depth. An increase in the impurity element concentrations was found at the surface of the AlN layer, as well as at the AlN—$WN_x$ interface. Impurities from these sections were excluded from the final compositional figures. TOF-ERDA experiments that are analogous to the ones described above were performed on samples lacking an AlN protective layer. These samples possessed oxygen to tungsten and hydrogen to tungsten ratios in the ranges of 0.51-0.88 and 0.48-0.53, respectively, whereas the carbon levels were nearly identical to those observed for the AlN-coated samples.

TABLE 1

Elemental composition (in atomic percent) of $WN_x$ thin films deposited by ALD as determined by TOF-ERDA.

| T (° C.) | W:N ratio | % W | % N | % C | % O | % H |
|---|---|---|---|---|---|---|
| 150 | 1.20 | 39 | 32 | 5 | 10 | 13 |
| 180 | 1.35 | 39 | 29 | 8 | 13 | 11 |
| 210 | 1.20 | 39 | 32 | 13 | 7 | 9 |
| Uncertainty | ±0.15 | ±4 | ±3 | ±4 | ±2 | ±3 |

Films grown at 180 and 210° C. without protective AlN overlayers were analyzed to determine their electrical resistivity values. These films were exposed to ambient atmosphere for approximately 12 to 24 hours prior to making the measurements. The film grown at 180° C. exhibited resistivity values of 4300 to 4600 microhm cm, while the film grown at 210° C. had resistivity values of 3500 to 3800 microhm cm. Further exposure of the same films to ambient atmosphere for an additional 30 days afforded resistivity values between 10,000 to 12,000 microhm cm.

Figure 4:
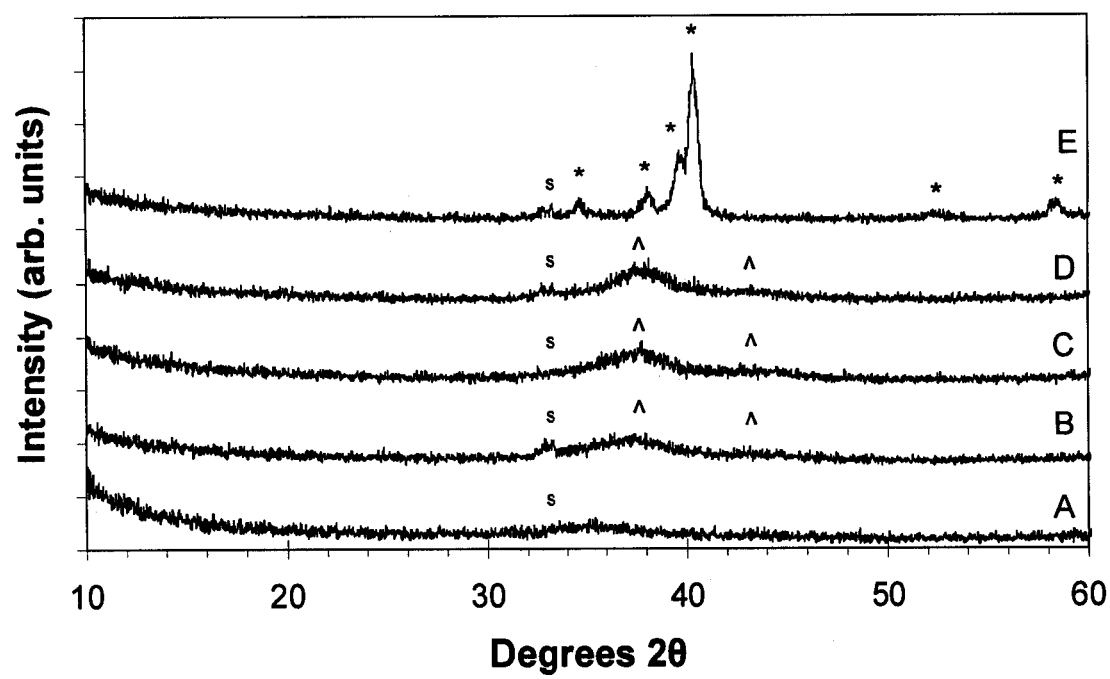
FIG. 4 provides X-ray diffraction patterns for WNx films: (A) as-deposited at 180° C., (B) annealed at 600° C., (C) annealed at 700° C., (D) annealed at 800° C., (E) annealed at 900° C. Diffraction patterns B-E were taken from samples of WNx deposited at 180° C. and then coated with a 50 nm thick AlN layer to prevent atmospheric oxidation. Reflections marked with s are from the substrate, those marked with ^ are due to cubic $W_2N$ (or possibly cubic AlN), and those marked.

X-ray diffraction (XRD) was performed on the deposited films to determine the presence and identity of any crystalline phases. Due to the air sensitivity of the films, diffraction experiments were carried out on annealed samples both with and without a protective AlN surface layer. XRD measurement of both sets of films grown at 180° C. showed no clear diffraction peaks, which indicates that the as-deposited films are amorphous. XRD experiments were performed on samples without the AlN overlayer that were annealed at various temperatures under a nitrogen atmosphere to assess the onset of crystallization. Upon heating an as-deposited film to 700° C., broad reflections were observed at 2q=23.1, 23.7, 24.4, 26.7, 28.9, 33.5, 34.1, 35.8, 41.9, 47.3, 50.8, 54.1, and 56.0°. The position and relative intensity of these reflections are consistent with the presence of tungsten oxide ($WO_3$) crystallites in this sample. Many polymorphs of $WO_3$ have been reported, which makes phase assignment of the observed diffraction pattern difficult. However, orthorhombic $WO_3$ (JCPDS 20-1324) appears to be the closest match, and the observed reflections correspond to the (001), (020), (200), (120), (111), (021), (201), (220), (221), (002), (112), (041), and (141) crystalline planes, respectively. Annealing of the same film to 800° C. led to an increase in the intensity and a slight decrease in the broadness of the above reflections. XRD experiments performed on annealed samples with an AlN protective overlayer gave a substantially different result (FIG. 4). Annealing to temperatures in the range of 600-800° C. produced very low intensity, broad reflections centered at 2θ=37.8 and 43.3°. These reflections are consistent with those expected for cubic $W_2N$ (JCPDS 25-1257), but are also consistent with cubic AlN (JCPDS 25-1495). Despite the fact that the two phases are difficult to distinguish, several points can be made: (1) prevention of air exposure to the tungsten nitride surface by means of the AlN overlayer prevents the formation of crystalline tungsten oxide phases at ≦800° C., (2) a likely source of the oxygen impurity is dioxygen or moisture from air, which can be inhibited by the AlN layer, and (3) at ≦800° C. the $WN_x$ present in the films is either amorphous (if the reflections are solely from AlN) or nanocrystalline. XRD performed on AlN-coated samples annealed at 900° C. provided reflections at 2q=34.7, 38.0, 39.6, 40.3, 52.4, and 58.4°. Although the reflections do not provide a reasonable match to any phases of material expected in the samples, the pattern does resemble cubic c-$Al_2O_3$ (JCPDS 4-880). The formation of $Al_2O_3$ is probably the result of reaction with either a small amount of oxygen impurity in the sample or trace dioxygen in the annealing furnace, since AlN is likely to be an efficient oxygen scavenger at 900° C.

The surface morphology of the as-deposited films was studied by atomic force microscopy (AFM). Micrographs of characteristic film surface features were collected for 70 nm thick tungsten nitride films deposited at 150, 180, and 210° C. Films deposited at each temperature were smooth and featureless. The root mean square (rms) surface roughnesses of typical 2 mm×2 mm areas were 0.9, 0.8, and 0.7 nm for films deposited at 150, 180, and 210° C., respectively.

Cross-sectional high resolution transmission electron microscopy (HRTEM) was performed to assess the morphology of a $WN_x$ thin film sample deposited at 180° C. using 200 deposition cycles. The film was completely amorphous with respect to crystallinity, and lacked any discernable short-range or long-range ordering in any of the collected images. Furthermore, the lack of regular contrast variations within the film suggests that the as-deposited $WN_x$ layer is of uniform density and does not possess any significant nanostructural features.

2. Molybdenum(II) and Tungsten(II) Complexes Containing Pyrazolato and Amidinato Ligands All reactions were carried out under argon using either glovebox or Schlenk line techniques. Toluene was distilled from sodium, tetrahydrofuran was distilled from sodium benzophenone ketyl, and hexane was distilled from $P_2O_5$. M(allyl)Cl(py)$_2$(CO)$_2$ (MoW), M(allyl)Cl(NCCH$_3$)$_2$(CO)$_2$, tBu$_2$pzK were prepared by literature procedures. 3,5-trifluoromethylpyrazole, methyllithium, 1,3-di-tert-butylcarbodiimide, 1,3-diisopropylcarbodiimide, and 1-tert-buty-3-ethyl-carbodiimide were purchased from Aldrich Chem. Co. and used as received.

1H, $^{13}C\{^1H\}$, and $^{19}F$ NMR were obtained in benzene-d$_6$ or toluene-d$_8$ on 500, 400, or 300 MHz spectrometers. Infrared spectra were obtained using Nujol as the medium. Elemental analyses were performed by Midwest Microlab, Indianapolis, Ind. Melting points were obtained with a Haake-Buchler HBI digital melting point apparatus and are uncorrected.

Preparation of Mo($\eta^3$-allyl)($\eta^2$-3,5-tBu$_2$pz)(py)(CO)$_2$ ("1a"). A 100-mL Schlenk flask, equipped with a magnetic stir bar and a rubber septum, was charged with Mo($\eta^3$-allyl)Cl(py)$_2$(CO)$_2$ (1.00 g, 2.59 mmol) and tBu$_2$pzK (0.571 g, 2.61 mmol) in tetrahydrofuran (40 mL). The resultant pale red solution was stirred at ambient temperature for 16 hours ("h"). The solvent was then removed under reduced pressure to yield a yellow crystalline solid. This solid was extracted with toluene (40 mL), and the resultant solution was filtered through a 2-cm pad of Celite on a coarse glass frit. The filtrate was concentrated to about 20 mL under reduced pressure and was placed in a −20° C. freezer for 36 hours. Decanting of the solvent followed by vacuum drying afforded brown crystals of 1a (0.932 g, 80%): m.p. 178-180° C.; IR (Nujol, cm$^{-1}$) 1941, 1842 ($\nu_{CO}$, s), 1600 (s), 1515 (m), 1498 (m), 1483 (s), 1416 (m), 1360 (s), 1312 (w), 1250 (m), 1231 (m), 1082 (w), 1066 (m), 1014 (s), 977 (m), 962 (w), 917 (w), 792 (s), 758 (s), 727 (w), 697 (s); $^1H$ NMR (benzene-d$_6$, 21° C.) 8.19 (d, J=4.9 Hz, 2H, H$_{2,6}$ of py), 6.54 (t, J=7.3 Hz, 1H, H$_4$ of py), 6.12 (t, J=7.3 Hz, 2H, H$_{3,5}$ of py), 6.00 (s, 1H, pz ring CH), 3.62 (tt, J=9.8 Hz, 1H, allyl-CH), 3.16 (d, J=6.7 Hz, 2H, allyl-CH$_2$), 1.34 (s, 18H, C(CH$_3$)$_3$), 1.29 (d, J=6.7 Hz, 2H, allyl-CH$_2$); $^{13}C\{^1H\}$ (benzene-d$_6$, 21° C., ppm) 231.86 (broad s, CO), 161.47 (s, CC(CH$_3$)$_3$), 150.94 (s, C$_{2,6}$ of py), 136.90 (s, C$_4$ of py), 124.06 (s, C$_{3,5}$ of py), 102.05 (s, pz ring CH), 73.44 (s, allyl-CH), 54.35 (s, allyl-CH$_2$), 32.26 (s, CC(CH$_3$)$_3$), 30.85 (s, CC(CH$_3$)$_3$); (Found: C, 55.73; H, 6.55; N, 9.49. C$_{21}$H$_{29}$MoN$_3$O$_2$ requires C, 55.87; H, 6.48; N, 9.31%).

Preparation of W($\eta^3$-allyl)($\eta^2$-3,5-tBu$_2$pz)(py)(CO)$_2$ ("1b"). In a fashion similar to the preparation of 1a, treatment of W($\eta^3$-allyl)Cl(py)$_2$(CO)$_2$ (1.00 g, 2.10 mmol) and tBu$_2$pzK (0.458 g, 2.10 mmol) in tetrahydrofuran (40 mL) afforded 1b as a yellow crystalline solid (0.883 g, 78%): m.p. 178-180° C.; IR (Nujol, cm$^{-1}$) 1931, 1828 ($\nu_{CO}$, s), 1601 (s), 1516 (w), 1500 (m), 1416 (w), 1362 (s), 1250 (m), 1232 (m), 1065 (m), 1015 (s), 995 (w), 796 (s), 759 (s), 727 (m), 695 (s); $^1H$ NMR (benzene-d$_6$, 21° C.) 8.29 (d, J=4.6 Hz, 2H, H$_{2,6}$ of py), 6.59 (t, J=7.3 Hz, 1H, H$_4$ of py), 6.18 (t, J=7.6 Hz, 2H, H$_{3,5}$ of py), 6.12 (s, 1H, pz ring CH), 3.02 (br, 2H, allyl-CH$_2$), 2.90 (tt, J=9.1 Hz, 1H, allyl-CH), 1.60 (br, 2H, allyl-CH$_2$), 1.340 (s, 18H, C(CH$_3$)$_3$); $^{13}C\{^1H\}$ (benzene-d$_6$, 21° C., ppm) 221.07 (br s, CO), 160.79 (s, CC(CH$_3$)$_3$), 151.44 (s, C$_{2,6}$ of py), 137.23 (s, C$_4$ of py), 124.53 (s, C$_{3,5}$ of py), 103.83 (s, pz ring CH), 65.00 (s, allyl-CH), 46.93 (s, allyl-CH$_2$), 32.36 (s, CC(CH$_3$)$_3$), 30.68 (s, CC(CH$_3$)$_3$); (Found: C, 46.69; H, 5.32; N, 7.88. C$_{21}$H$_{29}$N$_3$O$_2$W requires C, 46.77; H, 5.42; N, 7.79%).

Preparation of Mo($\eta^3$-allyl)[($\eta^1$-3,5-(CF$_3$)$_2$pz)(py)](CO)$_2$ ("2a"). In a fashion similar to the preparation of 1a, treatment of Mo($\eta^3$-allyl)Cl(py)$_2$(CO)$_2$ (1.00 g, 2.59 mmol) and (CF$_3$)$_2$pzK (0.651 g, 2.67 mmol) in tetrahydrofuran (40 mL) afforded 2a as a yellow crystalline solid (0.978 g, 68%): m.p. 145-147° C.; IR (Nujol, cm$^{-1}$) 1944, 1847 ($\nu_{CO}$, s), 1606 (s), 1518 (m), 1498 (m), 1445 (s), 1340 (m), 1260 (m), 1224 (m), 1143 (w), 1112 (s), 1073 (s), 1043 (m), 1001 (s), 977 (s), 882 (w), 810 (m), 760 (s), 704 (s); $^1H$ NMR (toluene-d$_8$, +80° C.) 8.50 (s, 4H, H$_{2,6}$ of py), 6.82 (t, J=7.3 Hz, 2H, H$_4$ of py), 6.74 (s, 1H, pz ring CH), 6.40 (t, J=6.7 Hz, 4H, H$_{3,5}$ of py), 4.08 (tt, J=9.8 Hz, 1H, allyl-CH), 3.04 (d, J=6.7 Hz, 2H, allyl-CH$_2$), 1.43 (d, J=6.7 Hz, 2H, allyl-CH$_2$); $^{13}C\{^1H\}$ (toluene-d$_8$, +80° C., ppm) 226.82 (s, CO), 153.20 (s, C$_{2,6}$ of py), 142.29 (q, $^2J_{CF}$=39 Hz), 137.27 (s, C$_4$ of py), 124.03 (d, C$_{3,5}$ of py), 121.53 (q, $^1J_{CF}$=270.2 Hz, CF$_3$), 104.91 (s, pz ring CH), 75.21 (s, allyl-CH), 61.08 (s, allyl-CH$_2$), $^{19}F$ NMR (toluene-d$_8$, 22° C., ppm) 127.51, 52.43 (s, CF$_3$); (Found: C, 43.34; H, 2.91; N, 10.11. C$_{20}$H$_{16}$F$_6$MoN$_4$O$_2$ requires C, 43.37; H, 3.02; N, 9.75%).

Preparation of W($\eta^3$-allyl)[($\eta^1$-3,5-(CF$_3$)$_2$pz)(py)](CO)$_2$ ("2b"). In a fashion similar to the preparation of 1a, treatment of W($\eta^3$-allyl)Cl(py)$_2$(CO)$_2$ (1.00 g, 2.10 mmol) and (CF$_3$)$_2$pzK (0.511 g, 2.10 mmol) in tetrahydrofuran (40 mL) afforded 2b as a yellow crystalline solid (1.35 g, 81%): m.p. 152-153° C.; IR (Nujol, cm$^{-1}$) 1937, 1852, 1826 ($\nu_{CO}$, s), 1607 (s), 1521 (m), 1499 (m), 1449 (m), 1342 (m), 1260 (m), 1225 (s), 1208 (m), 1160 (w), 1114 (s), 1069 (s), 1002 (s), 976 (m), 888 (w), 815 (m), 800 (m), 761 (s), 700 (s); $^1H$ NMR (toluene-d$_8$, +90° C.) 8.54 (br, s, 4H, H$_{2,6}$ of py), 6.87 (t, J=7.3 Hz, 2H, H$_4$ of py), 6.71 (s, 1H, pz ring CH), 6.40 (br, s, 4H, H$_{3,5}$ of py), 3.31 (tt, J=9.8 Hz, 1H, allyl-CH), 2.81 (br, s, 2H, allyl-CH$_2$), 1.75 (d, J=6.7 Hz, 2H, allyl-CH$_2$); $^{13}C\{^1H\}$ (toluene-d$_8$, +80° C., ppm) 217.75 (s, CO), 153.65 (s, C$_{2,6}$ of py), 142.21 (q, $^2J_{CF}$=39 Hz), 137.28 (s, C$_4$ of py), 124.44 (s, C$_{3,5}$ of py), 121.42 (q, $^1J_{CF}$=270.2 Hz, CF$_3$), 105.25 (s, pz ring CH), 66.50 (s, allyl-CH), 53.44 (s, allyl-CH$_2$), $^{19}F$ NMR (toluene-d$_8$, 22° C., ppm) 126.47, 52.43 (s, CF$_3$); (Found: C, 37.53; H, 2.53; N, 8.71. C$_{20}$F$_6$H$_{16}$N$_4$O$_2$W requires C, 37.41; H, 2.51; N, 8.72%).

Preparation of [Mo($\eta^3$-allyl)($\mu$-$\eta^1$:$\eta^2$-tBu$_2$pz(CO)$_2$]$_2$ ("3a"). In a fashion similar to the preparation of 1a, treatment of Mo($\eta^3$-allyl)Cl(NCCH$_3$)$_2$(CO)$_2$ (2.00 g, 6.43 mmol) and tBu$_2$pzK (1.42 g, 6.50 mmol) in tetrahydrofuran (40 mL) afforded 3a as a dark yellow crystalline solid (1.91 g, 79%): m.p. 200-202° C.; IR (Nujol, cm$^{-1}$) 1935, 1845 ($\nu_{CO}$, s), 1506 (m), 1500 (m), 1403 (m), 1363 (m), 1250 (m), 1212 (w), 1885 (w), 1026 (w), 1003 (m), 969 (s), 836 (s), 747 (w), 723 (w); $^1H$ NMR (toluene-d$_8$, 80° C.) 6.34 (s, 1H, pz ring CH), 3.63 (m, 1H, allyl-CH), 3.22 (d, J=7.3, 2H, allyl-CH$_2$), 1.340 (s, 18H, C(CH$_3$)$_3$), 1.09 (d, J=9.2, 2H, allyl-CH$_2$); $^{13}C\{^1H\}$ (toluene-d$_8$, 80° C., ppm) 234.01 (s, CO), 162.99 (s, CC(CH$_3$)$_3$), 109.03 (s, pz ring CH), 78.78 (s, allyl-CH), 54.59 (s, allyl-CH$_2$), 32.92 (s, CC(CH$_3$)$_3$), 30.54 (s, CC(CH$_3$)$_3$); (Found: C, 51.79; H, 6.34; N, 7.62. C$_{32}$H$_{46}$N$_4$O$_4$Mo$_2$ requires C, 51.76; H, 6.24; N, 7.54%).

Preparation of Mo($\eta^3$-allyl)[iPrNC(CH$_3$)NiPr](py)(CO)$_2$ ("4a"). A 100-mL Schlenk flask, equipped with a magnetic stir bar and a rubber septum, was charged with 1,3-diisopropylcarbodiimide (0.41 mL, 2.65 mmol) and THF (30 mL). To this stirred solution at ambient temperature was added 1.6 M solution of methyllithium in diethyl ether (1.66 mL, 2.66 mmol). The resultant colorless solution was stirred at ambient temperature for 2 hours. This solution was added by a cannula to a separate Schlenk flask that was cooled to −78° C. containing Mo($\eta^3$-allyl)Cl(py)$_2$(CO)$_2$ (1.00 g, 2.59 mmol) suspended in tetrahydrofuran (40 mL). The resultant orange-red solution was warmed to room temperature and stirred for 16 hours. The solvent was then removed under reduced pressure to yield a yellow crystalline solid. This solid was extracted with toluene (40 mL), and the resultant solution was filtered through a 2-cm pad of Celite on a coarse glass frit. The filtrate was concentrated to about 30 mL under reduced pressure and was placed in a −20° C. freezer for 36 hours. Decanting of the solvent followed by vacuum drying afforded yellow crystals of 4a (0.941 g, 87%): m.p. 125-127° C.; IR (Nujol, cm$^{-1}$) 1917, 1818 ($\nu_{CO}$, s), 1599 (s), 1501 (m), 1468 (s), 1441 (s), 1345 (m), 1317 (m), 1261 (w), 1219 (m), 1173 (m), 1143 (m), 1118 (m), 1068 (m), 1041 (w), 1019 (w), 918 (w), 810 (m), 759 (s), 700 (s); $^1$H NMR (toluene-d$_8$, 80° C.) 8.65 (m, 2H, H$_{2,6}$ of py), 6.93 (m, 1H, H$_4$ of py), 6.51 (m, 2H, H$_{3,5}$ of py), 3.77 (tt, J=9.4 Hz, 1H, allyl-CH), 3.42 (sep, J=6.3 Hz, 2H, CH(CH$_3$)$_2$), 3.06 (d, J=6.9 Hz, 2H, allyl-CH$_2$), 1.34 (s, 3H, C(CH$_3$)), 1.17 (d, J=6.2 Hz, 2H, allyl-CH$_2$), 1.08 (d, 12H, J=6.0 Hz, CH(CH$_3$)$_2$); $^{13}$C{$^1$H} (toluene-d$_8$, 21° C., ppm) 229.79 (s, CO), 168.91 (N$_2$CCH$_3$), 151.87 (s, C$_{2,6}$ of py), 136.87 (s, C$_4$ of py), 123.74 (s, C$_{3,5}$ of py) 68.69 (s, allyl-CH), 56.33 (s, allyl-CH$_2$), 48.15 (CH(CH$_3$)$_2$), 24.55 (CH(CH$_3$)$_2$), 10.33 (N$_2$CCH$_3$); (Found: C, 52.50; H, 6.46; N, 10.23. C$_{18}$H$_{27}$MoN$_3$O$_2$ requires C, 52.30; H, 6.58; N, 10.17%).

Preparation of W($\eta^3$-allyl)[iPrNC(CH$_3$)NiPr](py)(CO)$_2$ ("3b"). Treatment of W($\eta^3$-allyl)Cl(py)$_2$(CO)$_2$ (1.00 g, 2.10 mmol) with Li[iPrNC(CH$_3$)NiPr] (prepared from 1.6 M solution of methyllithium in diethyl ether (1.35 mL, 2.16 mmol) and 1,3-diispoproylcarbodiimide (0.32 mL, 2.10 mmol) in THF at −78° C. afforded 3b as a yellow crystalline solid (0.933 g, 79%): m.p. 153-155° C.; IR (Nujol, cm$^{-1}$) 1905, 1803 ($\nu_{CO}$, s), 1600 (s), 1502 (m), 1441 (s), 1348 (m), 1318 (m), 1261 (w), 1223 (m), 1174 (w), 1145 (m), 1119 (m), 1067 (m), 1042 (w), 1017 (w), 866 (w), 815 (m), 761 (s), 700 (s); $^1$H NMR (toluene-d$_8$, 80° C.) 8.74 (m, 2H, H$_{2,6}$ of py), 6.91 (m, 1H, H$_4$ of py), 6.48 (m, 2H, H$_{3,5}$ of py), 3.47 (sep, J=6.9 Hz, 2H, CH(CH$_3$)$_2$), 2.84 (br, 1H, allyl-CH), 2.84 (br, 2H, allyl-CH$_2$) (overlap of allyl-CH and —CH$_2$), 1.39 (d, J=6.0 Hz, 2H, allyl-CH$_2$), 1.28 (s, 3H, C(CH$_3$)), 1.07 (d, 12H, J=6.0 Hz, CH(CH$_3$)$_2$); $^{13}$C{$^1$H} (toluene-d$_8$, 21° C., ppm) 223.05 (s, CO), 169.49 (N$_2$CCH$_3$), 152.33 (s, C$_{2,6}$ of py), 137.05 (s, C$_4$ of py), 124.100 (s, C$_{3,5}$ of py), 60.08 (s, allyl-CH), 48.11 (s, br, allyl-CH$_2$), 48.11 (CH(CH$_3$)$_2$), 25.04, 23.58 (CH(CH$_3$)$_2$), 11.41 (N$_2$CCH$_3$); (Found: C, 43.52; H, 5.36; N, 8.25. C$_{18}$H$_{27}$N$_3$O$_2$W requires C, 43.13; H, 5.43; N, 8.38%).

Preparation of Mo($\eta^3$-allyl)[tBuNC(CH$_3$)NtBu](py)(CO)$_2$ ("5a"). In a fashion similar to the preparation of Xa, treatment of Mo($\eta^3$-allyl)Cl(py)$_2$(CO)$_2$ (1.00 g, 2.59 mmol) with Li[tBuNC(CH$_3$)NtBu] (0.456 g, 0.259 mmol) afforded 5a (0.835 g, 73%): m.p. 120-122° C.; IR (Nujol, cm$^{-1}$) 1912, 1811 ($\nu_{CO}$, s), 1602 (m), 1434 (m), 1411 (m), 1363 (m), 11226 (m), 1195 (s), 1154 (w), 1083 (w), 1070 (m), 1042 (m), 996 (w), 786 (w), 758 (s), 694 (s); $^1$H NMR (toluene-d$_8$, 21° C.) 9.037 (br, 2H, H$_{2,6}$ of py), 6.88 (m, 1H, H$_4$ of py), 6.54 (m, 2H, H$_{3,5}$ of py), 3.74 (tt, J=9.2 Hz, 1H, allyl-CH), 3.54 (br, 2H, allyl-CH$_2$), 1.66 (s, 3H, C(CH$_3$)), 1.29 (d, J=6.2 Hz, 2H, allyl-CH$_2$), 1.09 (s, 18H, C(CH$_3$)$_3$); $^{13}$C{$^1$H} (toluene-d$_8$, 21° C., ppm) 229.70 (s, CO), 171.11 (N$_2$CCH$_3$), 152.83 (s, C$_{2,6}$ of py), 137.55 (s, C$_4$ of py), 123.68 (s, C$_{3,5}$ of py), 72.82 (s, allyl-CH), 57.88 (s, C(CH$_3$)$_3$), 51.92 (s, allyl-CH$_2$), 33.03 (C(CH$_3$)$_3$), 20.96 (NCCH$_3$); (Found: C, 45.37; H, 5.93; N, 7.98. C$_{20}$H$_{31}$N$_3$O$_2$Mo requires C, 54.42; H, 7.08; N, 9.52%).

Preparation of W($\eta^3$-allyl)[tBuNC(CH$_3$)tBu](py)(CO)$_2$ ("4b"). Treatment of W($\eta^3$-allyl)Cl(py)$_2$(CO)$_2$ (1.73 g, 3.63 mmol) with Li[tBuNC(CH$_3$)tBu] afforded 4b as a yellow crystalline solid (1.71 g, 88%): m.p. 128-130° C.; IR (Nujol, cm$^{-1}$) 1913, 1812 ($\nu_{CO}$, s), 1602 (s), 1443 (m), 1411 (m), 1362 (m), 1226 (m), 1195 (s), 1153 (m), 1082 (w), 1070 (m), 1042 (m), 758 (m), 694 (s); $^1$H NMR (toluene-d$_8$, +80° C.) 9.10 (d, J=5.5 Hz, 2H, H$_{2,6}$ of py), 6.99 (t, J=5.5 Hz, 1H, H$_4$ of py), 6.64 (t, J=6.1 Hz, 2H, H$_{3,5}$ of py), 3.24 (d, J=6.1 Hz, 2H, allyl-CH$_2$), 2.87 (m, 1H, allyl-CH), 1.65 (s, 3H, C(CH$_3$)), 1.47 (d, J=8.7 Hz, 2H, allyl-CH$_2$), 1.12 (s, 3H, C(CH$_3$)); $^{13}$C{$^1$H} (toluene-d$_8$, 21° C., ppm) 223.77 (s, CO), 172.75 (NCCH$_3$), 153.21 (s, C$_{2,6}$ of py), 138.18 (s, C$_4$ of py), 124.16 (s, C$_{3,5}$ of py), 66.63 (s, allyl-CH), 51.89 (br, s, C(CH$_3$)$_3$), 50.61 (br, s, 32.95 (C(CH$_3$)$_3$), 23.18 (NCCH$_3$); (Found: C, 45.37; H, 5.93; N, 7.98. C$_{20}$H$_{31}$N$_3$O$_2$W requires C, 45.38; H, 5.90; N, 7.94%).

Preparation of W($\eta^3$-allyl)[tBuNC(CH$_3$)NtBu] (CO)$_2$ ("5b"). Treatment of W($\eta^3$-allyl)Cl(py)$_2$(CO)$_2$ (1.73 g, 3.63 mmol) with Li[tBuNC(CH$_3$)NtBu] afforded 5b as a yellow crystalline solid. Sublimation of the crude product at 100° C./0.03 torr afforded xb (0.40 g, 21%) and red crystals (xb) (0.11 g, 7%): m.p. 178-180° C.; IR (Nujol, cm$^{-1}$) 1922, 1823 ($\nu_{CO}$, s), 1600 (br, w), 1420 (m), 1365 (s), 1233 (m), 1194 (s), 1101 (m), 1036 (w), 1009 (m), 889 (w), 797 (m); $^1$H NMR (toluene-d$_8$, −80° C.) 2.67 (d, J=6.6 Hz, 2H, allyl-CH$_2$), 2.55 (m, 1H, allyl-CH), 1.50 (s, 3H, C(CH$_3$)), 1.18 (s, 18H, C(CH$_3$)$_3$), 1.10 (d, J=9.9 Hz, 2H, allyl-CH$_2$); $^{13}$C{$^1$H} (toluene-d$_8$, 21° C., ppm) 230.26 (s, CO), 160.82 (N$_2$CCH$_3$), 65.77 (s, allyl-CH), 55.12 (s, C(CH$_3$)$_3$), 44.41 (s, allyl-CH$_2$), 31.47 (C(CH$_3$)$_3$), 20.18 (NCCH$_3$).

Preparation of W$_2$(NMe$_2$)$_4$(tBu$_2$pz)$_4$ ("7"). A 100-mL Schlenk flask, equipped with a magnetic stir bar and a rubber septum, was charged with W(NMe$_2$)$_6$ (1.00 g, 1.58 mmol), tBu$_2$pzH (0.571 g, 3.16 mmol), and toluene (40 mL). The resultant yellow/red solution was refluxed for 8 hours and was then placed in a −20° C. freezer for 36 hours. Decanting of the solvent followed by vacuum drying afforded 7 yellow crystals (1.76 g, 81%): m.p. 265-267° C. (dec); $^1$H NMR (toluene-d$_8$, −80° C., δ) 6.52 (s, 2H, pz ring CH), 4.81, 4.65, 2.58, 2.322 (s, 24H, N(CH$_3$)$_2$), 1.58, 1.23 (s, 36H, C(CH$_3$)$_3$); (Found: C, 40.22; H, 6.92; N, 12.42. C$_{30}$H$_{62}$N$_8$W$_2$ requires C, 39.92; H, 6.71; N, 12.39%).

Preparation of Mo[iPrNC(CH$_3$)iPr]$_3$ ("8"). A 100-mL Schlenk flask, equipped with a magnetic stir bar and a rubber septum, was charged with MoCl$_3$(THF)$_3$ (0.501 g, 1.34 mmol) and diethyl ether (40 mL). To this stirred solution at −78° C. was added a suspension of 1,3-diisopropylacetamidinateolithium (prepared from 1,3-diidopropylcarbodiimide (0.63 mL, 1.01 mmol) and 1.6 M solution of methyllithium in diethyl ether (2.53 mL, 1.01 mmol)). The resultant solution was stirred at ambient temperature for 16 hours. The solvent was then removed under reduced pressure to yield a yellow crystalline solid which was extracted with 40 mL of hexane. The hexane extract was filtered through a 2-cm pad of Celite on a coarse glass frit. The filtrate was placed in a −25° C. freezer to afford 8 as yellow crystals (0.48 g, 65%): m.p. >300° C.; IR (Nujol, cm$^{-1}$) 2598 (w), 1355 (s), 1220 (s), 1174 (s), 1145 (s), 1120 (m), 1050 (m), 1012 (s), 812 (m), 721 (w), 797 (s); $^1$H NMR (C$_6$D$_6$, 22° C., δ) 1.31 (s, broad), 0.89 (s, broad), 4.62 (s, broad).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formulae 1 or 2:

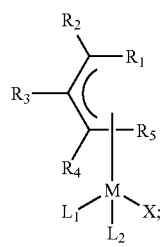

1

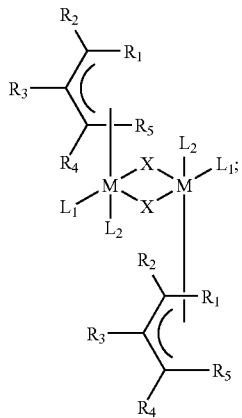

2 wherein $R_1$, $R_2$, $R_3$, $R_4$, and $R_5$ are each independently alkyl, aryl, arylalkyl, hydrogen, and silyl;

$L_1$, $L_2$ are each independently a neutral donor ligand;

X is a monoanionic nitrogen donor ligand; and

M is molybdenum or tungsten.

2. The compound of claim 1 wherein $R_1$, $R_2$, $R_3$, $R_4$, and $R_5$ are each independently alkyl or hydrogen.

3. The compound of claim 1 wherein $R_1$, $R_2$, $R_3$, $R_4$, and $R_5$ are each hydrogen.

4. The compound of claim 1 wherein $L_1$, $L_2$ are each carbon monoxide.

5. The compound of claim 1 wherein X is

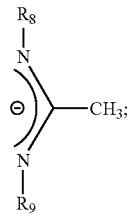

3

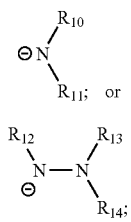

4

5

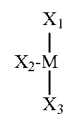

6 wherein $R_6$, $R_7$, $R_8$, $R_9$, $R_{10}$, $R_{11}$, $R_{12}$, $R_{13}$, and $R_{14}$ are each independently hydrogen or alkyl.

6. The compound of claim 5 wherein $R_6$, $R_7$, $R_8$, $R_9$, $R_{10}$, $R_{11}$, $R_{12}$, $R_{13}$, and $R_{14}$ are hydrogen.

7. The compound of claim 5 wherein $R_6$, $R_7$, $R_8$, $R_9$, $R_{10}$, $R_{11}$, $R_{12}$, $R_{13}$, and $R_{14}$ are each independently hydrogen, —$CF_3$, isopropyl, or t-butyl.

8. A method for making a metal nitride coating on a substrate by heating the compound of claim 1, the method comprising:

a) heating a compound having formula 1 or 2 to a sufficient temperature to form the metal nitride coating.

9. A method for making a metal nitride coating on a substrate by heating the compound of claim 1, the method comprising:

a) contacting the substrate with a compound having formula 1 or 2; and b) heating the compound having formula 1 or 2 to a sufficient temperature to form the metal nitride coating.

10. A compound having formula 7 or 8:

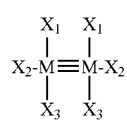

7

8 wherein $X_1$, $X_2$, and $X_3$ are each independently

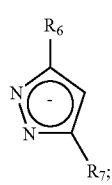

3

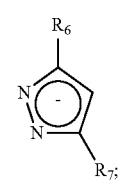

3

-continued

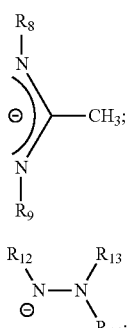

$R_6$, $R_7$, $R_8$, $R_9$, $R_{10}$, $R_{11}$, $R_{12}$, $R_{13}$, and $R_{14}$ are each independently hydrogen or alkyl; and M is molybdenum or tungsten.

11. The compound of claim 10 wherein $R_6$, $R_7$, $R_8$, $R_9$, $R_{10}$, $R_{11}$, $R_{12}$, $R_{13}$, and $R_{14}$ are hydrogen.

12. The compound of claim 10 wherein $R_6$, $R_7$, $R_8$, $R_9$, $R_{10}$, $R_{11}$, $R_{12}$, $R_{13}$, and $R_{14}$ are each independently hydrogen, —$CF_3$, isopropyl, or t-butyl.

13. A method for making a metal nitride coating on a substrate by heating the compound of claim 10, the method comprising:

a) heating a compound having formula 7 or 8 to a sufficient temperature to form the metal nitride coating.

14. A method for making a metal nitride coating on a substrate by heating the compound of claim 10, the method comprising:

a) contacting the substrate with a compound having formula 7 or 8; and b) heating the compound having formula 7 or 8 to a sufficient temperature to form the metal nitride coating.

15. A compound having formula 7 or 8:

$$X_2-M\begin{matrix}X_1\\|\\|\\X_3\end{matrix} \quad 7$$

$$X_2-\underset{\underset{X_3}{|}}{\overset{\overset{X_1}{|}}{M}}\equiv\underset{\underset{X_3}{|}}{\overset{\overset{X_1}{|}}{M}}-X_2 \quad 8$$

wherein $X_1$, $X_2$, and $X_3$ are each independently $$\ominus\underset{\diagdown R_{11}}{\overset{\diagup R_{10}}{N}}; \quad 5$$

or $R_6$, $R_7$, $R_8$, $R_9$, $R_{10}$, $R_{11}$, $R_{12}$, $R_{13}$, and $R_{14}$ are each independently hydrogen, —$CF_3$, isopropyl, or t-butyl; and M is molybdenum or tungsten.

* * * * *